(12) United States Patent
Mauduit et al.

(10) Patent No.: US 8,299,250 B2
(45) Date of Patent: Oct. 30, 2012

(54) CHIRAL TRIDENTATE COMPOUNDS, CORRESPONDING ORGANOMETAL COMPLEXES, METHOD FOR PREPARING SAME AND USE OF SAID COMPOUNDS AND COMPLEXES AS LIGANDS IN ASYMMETRICAL CATALYSIS

(75) Inventors: Marc Mauduit, Vitre (FR); Diane Rix, Rennes (FR); Christophe Crevisy, Pont-Pean (FR); Joanna Wencel, Cesson-Sevigne (FR)

(73) Assignees: Ecole Nationale Supérieure de Chimie de Rennes, Cedex (FR); CNRS (Centre National de la Recherche Scientifique), Cedex (FR)

( * ) Notice: Subject to any disclaimer, the term of this patent is extended or adjusted under 35 U.S.C. 154(b) by 10 days.

(21) Appl. No.: 12/738,326

(22) PCT Filed: Oct. 17, 2008

(86) PCT No.: PCT/EP2008/064067
§ 371 (c)(1),
(2), (4) Date: Jul. 2, 2010

(87) PCT Pub. No.: WO2009/050284
PCT Pub. Date: Apr. 23, 2009

(65) Prior Publication Data
US 2010/0267956 A1    Oct. 21, 2010

(30) Foreign Application Priority Data
Oct. 18, 2007 (FR) .................................... 07 58420

(51) Int. Cl.
*C07D 215/12* (2006.01)
*C07F 9/50* (2006.01)
*C07F 19/00* (2006.01)

(52) U.S. Cl. ............ 546/10; 546/174; 546/176; 556/19; 556/562; 562/440

(58) Field of Classification Search ........................ None
See application file for complete search history.

(56) References Cited

OTHER PUBLICATIONS

F. Zaragoza Dorwald, Side Reactions in Organic Synthesis; A Guide to Successful Synthesis Design, Wiley-VCH, Weinheim, Preface, p. IX (2005).*
Ankersmit et al., Methyl-, Acetyl-, and Allyl-Palladium and -Platinum Complexes Containing Novel Terdentate PNS and NN's Ligands, 252(1-2) Inorganic Chimica Acta 339-354 (1996) (CAS Abstracts (Nov. 2, 2011)).*
Brunner et al., Asymmetric Catalysis. Part 115. Enantioselective Palladium-Catalyzed Allylation of 1,5-Dimethylbarbituric Acid, (1) European J. Inorg. Chem. 43-54 (1998) (CAS Abstracts (Nov. 2, 2011)).*
Wencel et al., Chiral Phosphinoazomethinylate Salts as New 'One-Step Available' Ligands for Copper-Catalyzed Asymmetric Conjugate Addition, 19 Tetrahedron: Asymmetry 1804-1809 (2008).*
Degrado, et al.; Efficient Cu-Catalyzed Asymmetric Conjugate Additions of Alkylzincs to Trisubstituted Cyclic Enones; J. Am. Chem. Soc. 13362; 2002; 124, 13362-13363.
Brunner, et al.; Asymmetric Catalysis, 125[≠] Synthesis of the Stereoisomers of Methohexital by Palladium-Catalyzed Allylation; Eur. J. Inorg. Chem. 1999, 51-59.
Luchaco-Cullis; Cu-Catalyzed Enantioselective Conjugate Addition of Alkylzincs to Cyclic Nitroalkenes: Catalytic Asymmetric Synthesis of a Cyclic α-Substituted Ketones; J. Am. Chem. Soc.; 8192; 2002, 124, 8192-8193.
Mizutani, et al.; Cu-Catalyzed Asymmetric Conjugate Additions of Alkylzinc Reagents to Acyclic Aliphatic Enones; J. Am. Chem. Soc., vol. 124, No. 5, 2002; 779-781. Josephsohn, et al.; Efficient and Practical Ag-Catalyzed Cycloadditions Between Arylimines and the Danishefsky Diene; 4018; J. Am. Chem. Soc.; 2003, 125, 4018-4019.
Carswell, et al.; A Highly Efficient and Practical Method for Catalytic Asymmetric Vinylogous Mannich (AVM) Reactions; Angew. Chem. Int. Ed. 2006; 45, 7230-7233.
Ferioli, et al.; Steric Effects in Enantioselective Allylic Alkylation Catalysed by Cationic (η3-Allyl)palladium Complexes Bearing Chiral Pyridine-Aziridine Ligands; Eur. J. Org. Chem. 2005, 1416-1426.

* cited by examiner

*Primary Examiner* — Janet Andres
*Assistant Examiner* — Timothy R. Rozof
(74) *Attorney, Agent, or Firm* — Thomas, Kayden, Horstemeyer & Risley, LLP

(57) ABSTRACT

The invention relates to a compound of the formula (I) or the formula (II) in which: W is an oxygen atom or a radical of the formula NH; X is hydrogen or an alkaline cation or a C1-C8 alkyl or a $-(CH_2)_n{}^3-C(R^4)(R^5)(R^6)$ radical; X and R on the one hand and X and $R^1$ on the other hand may independently form an optionally substituted cycle with 5, 6 or 7 links. The invention also relates to complexes of said compounds with at least one metal selected from the group comprising copper, palladium, ruthenium, iridium and rhodium, and to a method for the synthesis of these compounds. These compounds and complexes can be used in various asymmetrical catalysis methods.

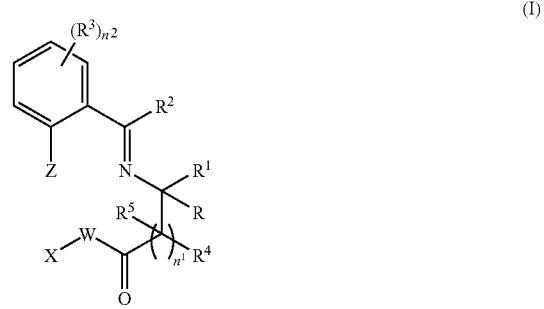

(I)

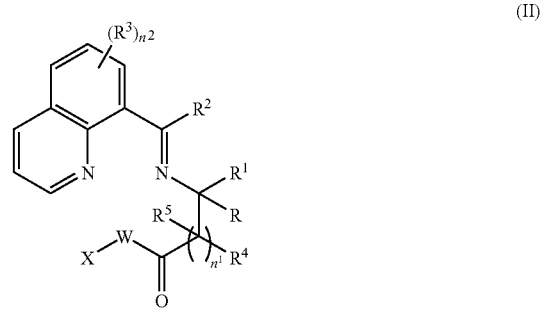

(II)

6 Claims, No Drawings

CHIRAL TRIDENTATE COMPOUNDS, CORRESPONDING ORGANOMETAL COMPLEXES, METHOD FOR PREPARING SAME AND USE OF SAID COMPOUNDS AND COMPLEXES AS LIGANDS IN ASYMMETRICAL CATALYSIS

CROSS REFERENCE TO RELATED APPLICATION

This application claims priority to PCT Application entitled "Chiral Tridentate Compounds, Corresponding Organometal Complexes, Method for Preparing the Same and Use of Said Compounds and Complexes as Ligands in Asymmetrical Catalysis," having serial number PCT/EP2008/064067, filed on Oct. 17, 2008, which claims priority to and benefit of French Application No. 0758420, filed on Oct. 18, 2007, which is incorporated by reference in its entirety.

The field of the invention is that of catalyst chemistry.

More specifically, this invention relates to new chiral tridentate compounds having an azomethine-type structure.

The invention also relates to metallo-azomethinylate-type organometal complexes obtained by complexing such compounds with various transition metals, in particular copper, palladium, ruthenium, iridium and rhodium.

The invention also relates to the use of such compounds or complexes in asymmetric catalysis methods implementing various transition metals such as, in particular, but not exclusively, enantioselective catalysis methods of conjugate addition, hydrogenation, C—H activation, isomerization, and C—C and C—N bonding.

This invention also relates to a method of synthesizing such compounds and in particular the synthesis of chiral azomethinylate diphenylphosphinoaryl and quinoline salts from enantiomerically-enriched α- and β-amino carboxylic acids and diversely-substituted aromatic aldehydes.

An objective of this invention is to propose new tridentate ligands that can quickly be accessed from a highly-diversified chiral source available on the market at low cost, namely α- and β-amino carboxylic acids.

Another objective of the invention is to describe such new ligands and the complexes associated with them capable of having excellent reactivity and enantioselectivity in asymmetric catalysis involving various transition metals.

The invention relates to any compound of formula (I) or (II):

(I)

(II)

in which:

W is an oxygen atom or a radical with the formula NH;

X is a hydrogen, or an alkaline cation, or a C1 to C8 alkyl, or a $-(CH_2)_{n^3}-C(R^4)(R^5)(R^6)$ radical in which $R^4$, $R^5$ and $R^6$ are independently a hydrogen, or a C1 to C8 alkyl, or a C5 or C6 cycloalkyl or an aryl or a naphthyl, optionally substituted; X and R on the one hand and X and $R^1$ on the other hand can independently form a ring with 5, 6 or 7 chains, optionally substituted;

$n^3 = 0$ or 1;

$n^1 = 0$ or 1 or 2;

$n^2 = 0$ to 4;

R and $R^1$ are independently a C1 to C8 alkyl, an optionally substituted C5 or C6 cycloalkyl, or an optionally substituted naphthyl, or a $-(CH_2)_{n^4}-C(R^9)(R^{10})V$ radical in which $R^9$ and $R^{10}$ are independently a hydrogen, or a C1 to C6 alkyl, or a C5 or C6 cycloalkyl, or an aryl; R and $R^4$ on the one hand and $R^1$ and $R^4$ on the other hand can independently form a ring with 3, 4, 5, 6 or 7 chains, optionally substituted; R and $R^5$ on the one hand and $R^1$ and $R^5$ on the other hand can independently form a ring with 3, 4, 5, 6 or 7 chains, optionally substituted;

V is a radical with the formula:

$(CH_2)_{n^5}Y$

Y is a hydrogen, or a halogen, or an $OR^{11}$, or a $SR^{12}$, or a $COOR^{13}$, or a $NHCOR^{14}$, or a C5 or C6 cycloalkyl, or an optionally substituted aryl;

$n^4 = 0$ or 1;

$n^5 = 1$ to 6;

$R^2$ is a hydrogen, or a C1 to C8 alkyl, or an optionally substituted aryl or a naphthyl;

$R^3$ is a C1 to C6 alkyl, or a halogen, or an $OR^{15}$;

Z is a radical with the formula $P(R^{16})_2$, or a radical with the formula $SR^{17}$, or a radical with the formula $OR^{18}$, or a radical with the formula $P(O)R^{19}$, or a radical with the formula $SO_2R^{20}$, or a radical with the formula $NR^{21}_2$;

$R^{11}$, $R^{12}$, $R^{13}$, $R^{14}$, $R^{15}$, are independently a H, or a C1 to C6 alkyl, or a C5 or C6 cycloalkyl or an optionally substituted aryl;

$R^{16}$, $R^{17}$, $R^{18}$, $R^{19}$, $R^{20}$, $R^{21}$ are independently a C1 to C6 alkyl, or a C6 cycloalkyl, or an aryl.

According to an alternative, the compound is a diphenyl phosphinophenyl azomethinylate, such as, in particular, a compound with the formula Ia-K, Ia-Na or Ib-K:

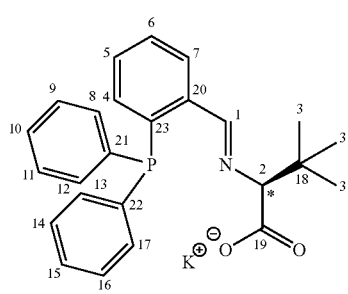

Ia-K

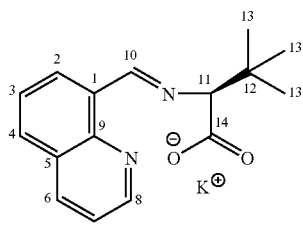

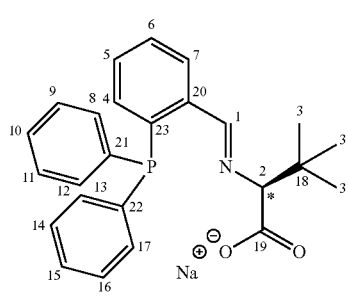

Ia-Na

IIa-K

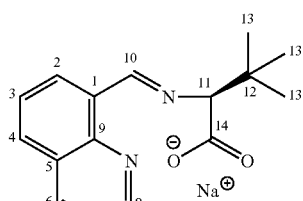

IIa-Na

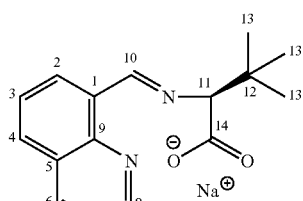

The invention also relates to any complex of a compound as described above with at least one metal chosen from the group consisting of copper, palladium, ruthenium, iridium and rhodium, such as, in particular, a complex with the formula:

III-Cu

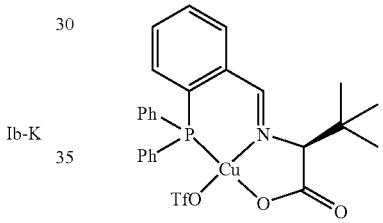

Ib-K

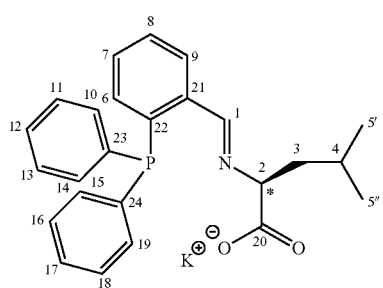

The invention also relates to a method for synthesizing a compound as described above, characterized in that it includes steps consisting of:

obtaining a product of formula A from an amino carboxylic acid:

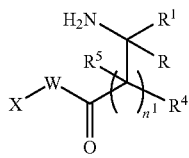

According to another embodiment, it is a compound with the formula Ic.

adding, to the product obtained, an aldehyde or a ketone chosen from the group of aldehydes or ketones of formula B:

Ic

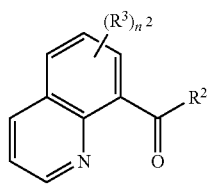

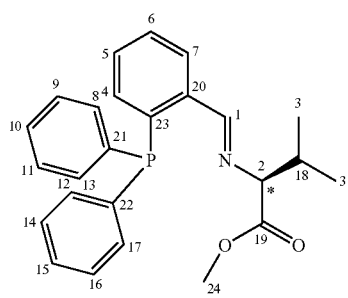

According to another alternative, the compound according to the invention is a quinoline-azomethinylate, such as, in particular, a compound with the formula IIa-K or IIa-Na.

and aldehydes or ketones of formula C:

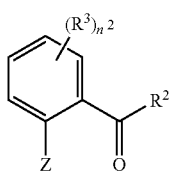

According to an alternative, said aldehyde is chosen from the group consisting of diphenylphosphine-benzaldehyde and quinoline-8 carboxaldehyde.

For the compounds described above of formula Ia-K or Ia-Na or IIa-K or IIa-Na, the method according to the invention preferably involves a reaction pattern chosen from the following group of reaction patterns:

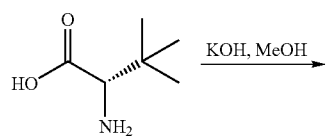

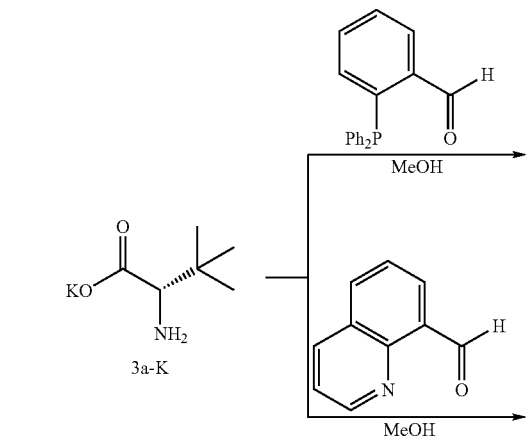

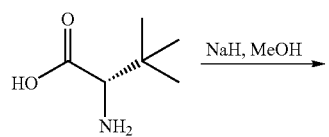

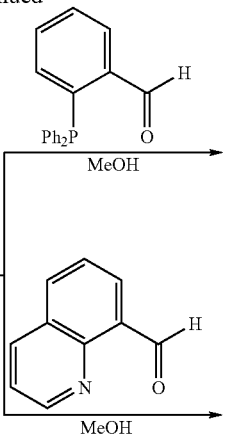

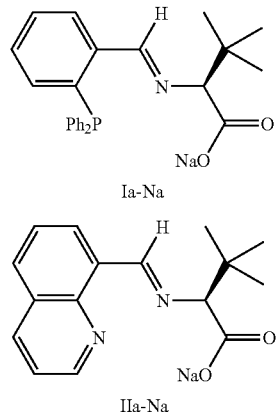

Finally, this invention also relates to any use of a compound or a complex as described above in an asymmetric catalysis method.

The invention as well as the various advantages thereof can be more easily understood with the following description of various embodiments of compounds and a complex according to the invention, as well as with the description of the use thereof in various asymmetric catalysis methods.

The synthesis of two examples of compounds of formula (I), namely diphenylphosphinophenyl-azomethinylate sodium and potassium salts obtained from tert-leucine (Ia-Na et Ia-K) and the synthesis of two examples of compounds of formula (II), namely quinoline-azomethinylate sodium and potassium salts obtained from tert-leucine (IIa-Na and IIa-K) are described in detail below.

These syntheses have the synthesis patterns shown below:

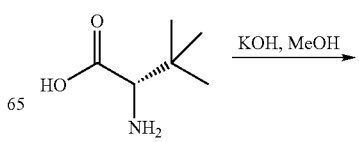

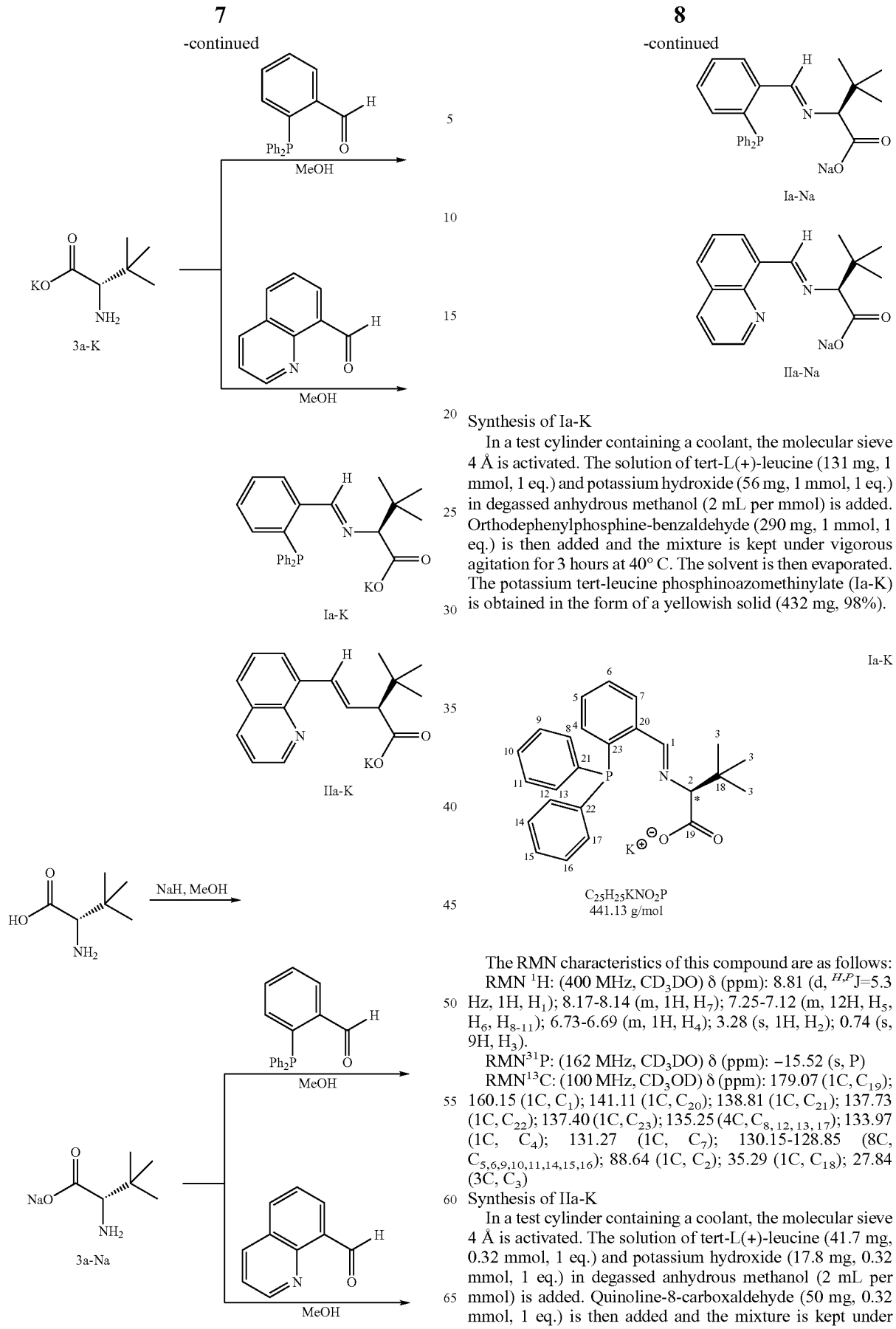

Synthesis of Ia-K

In a test cylinder containing a coolant, the molecular sieve 4 Å is activated. The solution of tert-L(+)-leucine (131 mg, 1 mmol, 1 eq.) and potassium hydroxide (56 mg, 1 mmol, 1 eq.) in degassed anhydrous methanol (2 mL per mmol) is added. Orthodephenylphosphine-benzaldehyde (290 mg, 1 mmol, 1 eq.) is then added and the mixture is kept under vigorous agitation for 3 hours at 40° C. The solvent is then evaporated. The potassium tert-leucine phosphinoazomethinylate (Ia-K) is obtained in the form of a yellowish solid (432 mg, 98%).

The RMN characteristics of this compound are as follows:

RMN $^1$H: (400 MHz, CD$_3$DO) δ (ppm): 8.81 (d, $^{H,P}$J=5.3 Hz, 1H, H$_1$); 8.17-8.14 (m, 1H, H$_7$); 7.25-7.12 (m, 12H, H$_5$, H$_6$, H$_{8-11}$); 6.73-6.69 (m, 1H, H$_4$); 3.28 (s, 1H, H$_2$); 0.74 (s, 9H, H$_3$).

RMN$^{31}$P: (162 MHz, CD$_3$DO) δ (ppm): −15.52 (s, P)

RMN$^{13}$C: (100 MHz, CD$_3$OD) δ (ppm): 179.07 (1C, C$_{19}$); 160.15 (1C, C$_1$); 141.11 (1C, C$_{20}$); 138.81 (1C, C$_{21}$); 137.73 (1C, C$_{22}$); 137.40 (1C, C$_{23}$); 135.25 (4C, C$_{8,12,13,17}$); 133.97 (1C, C$_4$); 131.27 (1C, C$_7$); 130.15-128.85 (8C, C$_{5,6,9,10,11,14,15,16}$); 88.64 (1C, C$_2$); 35.29 (1C, C$_{18}$); 27.84 (3C, C$_3$)

Synthesis of IIa-K

In a test cylinder containing a coolant, the molecular sieve 4 Å is activated. The solution of tert-L(+)-leucine (41.7 mg, 0.32 mmol, 1 eq.) and potassium hydroxide (17.8 mg, 0.32 mmol, 1 eq.) in degassed anhydrous methanol (2 mL per mmol) is added. Quinoline-8-carboxaldehyde (50 mg, 0.32 mmol, 1 eq.) is then added and the mixture is kept under vigorous agitation for 3 hours at 40° C. The solvent is then evaporated. The potassium tert-leucine quinoleinezomethinylate (IIa-K) is obtained in the form of a brown solid (96 mg, 97%).

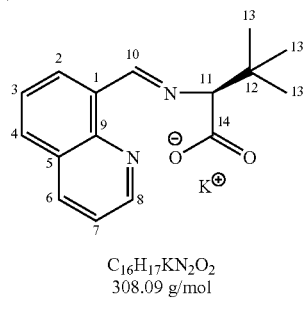

IIa-K $C_{16}H_{17}KN_2O_2$
308.09 g/mol

The RMN characteristics of this compound are as follows:
RMN $^1$H: (400 MHz, $CD_3DO$) δ (ppm): 9.47 (s, 1H, $H_{10}$); 8.91 (d, $^2J$=2.6, 1H, $H_8$); 8.55 (d, $^2J$=7.0, 1H, $H_6$); 8.3 (d, $^2J$=8.1, 1H, $H_4$); 8.00 (d, $^2J$=7.9, 1H, $H_2$); 7.67 (t, $^2J$=7.7, 1H, $H_3$); 7.53 (dd, $^2J$=4.0, $^2J$=8.4, 1H, $H_7$); 3.76 (s, 1H, $H_{11}$); 1.11 (s, 9H, $H_{13}$)

RMN $^{13}$C: (100 MHz, $CD_3DO$) δ (ppm): 179.52 (1C, $C_{14}$); 159.66 (1C, $C_{10}$); 151.36 (1C, $C_8$); 147.67 (1C, $C_9$); 137.95 (1C, $C_1$); 134.17 (1C, $C_6$); 131.62 (1C, $C_2$); 129.88 (1C, $C_4$); 129.77 (1C, $C_5$); 127.63 (1C, $C_7$); 122.56 (1C, $C_3$); 88.97 (1C, $C_{11}$); 35.49 (1C, $C_{12}$); 28.11 (3C, $C_{13}$).

Synthesis of Ia-Na
A synthesis method similar to that used for the synthesis of compound Ia-K was implemented, using sodium hydroxide instead of potassium hydroxide.

Synthesis of IIa-Na
A synthesis method similar to that used for the synthesis of compound IIa-K was implemented, using sodium hydroxide instead of potassium hydroxide.

According to another embodiment, the synthesis of compound Ib-K was also performed.

Synthesis of Ib-K
In a test cylinder containing a coolant, the molecular sieve 4 Å is activated. The solution of L(+)-leucine (65.5 mg, 0.5 mmol, 1 eq.) and potassium hydroxide (28 mg, 0.5 mmol, 1 eq.) in degassed anhydrous methanol (2 mL per mmol) is added. Orthodiphenylphosphine-benzaldehyde (145 mg, 0.5 mmol, 1 eq.) is then added and the mixture is kept under vigorous agitation for 3 hours at 40° C. The solvent is then evaporated. The potassium iso-leucine phosphinoazomethinylate (Ib-K) is obtained in the form of a yellowish solid (209 mg, 95%).

Ib-K

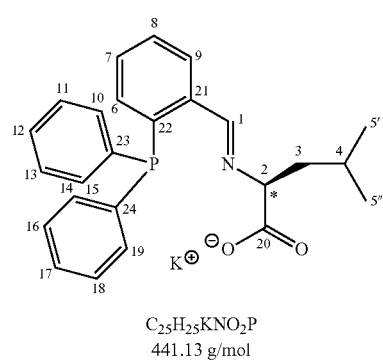

$C_{25}H_{25}KNO_2P$
441.13 g/mol

The RMN characteristics of this compound are as follows:
RMN $^1$H: (400 MHz, $CD_3DO$) δ (ppm): 8.88 (d, $^{H,P}J$=5.5 Hz, 1H, $H_1$); 8.06-8.02 (m, 1H, $H_9$); 7.28-7.07 (m, 12H, $H_7$, $H_8$, $H_{10-19}$); 6.72-6.69 (m, 1H, $H_5$); 3.70 (dd $^2J$=4.4 Hz, $^2J$=9.7 Hz, 1H, $H_2$); 1.55 (qd, $^3J$=4.4 Hz, $^2J$=9.7 Hz, 2H, $H_3$); 0.89 (m, 1H, $H_4$); 0.62 (d, $^3J$=6.6 Hz, 3H, $H_{5'}$); 0.51 (d, $^3J$=6.4 Hz, 3H, $H_{5''}$)

RMN $^{31}$P: (162 MHz, $CD_3DO$) δ (ppm): −14.59 (s, 1P)

RMN $^{13}$C: (100 MHz, $CD_3DO$) δ (ppm): 180.90 (1C, $C_{20}$); 161.59 (1C, $C_1$); 141.42 (1C, $C_{21}$); 139.32 (1C, $C_{24}$); 139.13 (1C, $C_{23}$); 138.0 (1C, $C_6$); 137.74 (1C, $C_{22}$); 135.8 (4C, $C_{10,14,15,19}$) 134.33 (1C, $C_9$); 131.87-129.13 (8C, $C_{7,8,11-13,16-18}$); 76.94 (1C, $C_2$); 44.54 (1C, $C_4$); 25.7 (1C, $C_{5''}$); 24.3 (1C, $C_{5'}$); 21.9 (1C, $C_3$)

According to another embodiment, the synthesis of phosphinoazomethinylate valine methyl ester Ic was performed.

Synthesis of Phosphinoazomethinylate Valine Methyl Ester Ic

Ic

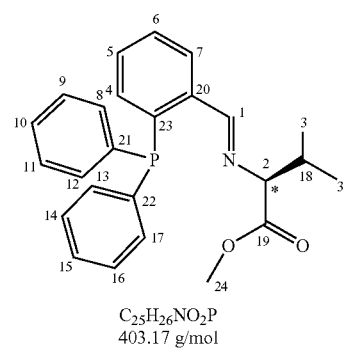

$C_{25}H_{26}NO_2P$
403.17 g/mol 500 mg of methyl ester of L-(+)-valine hydrochloride are placed in a round-bottom flask. 45 mL of buffer solution ($K_2HPO_4/K_3PO_4$ (pH=12.4)), then 22.5 mL of anhydrous dichloromethane are successively added. The mixture is agitated at room temperature for 30 min. The organic phase is separated, washed with brine, dried on magnesium sulfate, filtered and concentrated under vacuum.

In a test cylinder containing a coolant, the molecular sieve 4 Å is activated. The solution of L(+)-valine methyl ester (45.27 mg, 0.34 mmol, 1 eq.) in degassed anhydrous methanol (2 mL per mmol) is added. Orthodiphenylphosphine-benzaldehyde (100 mg, 0.34 mmol, eq.) is then added and the mixture is kept under vigorous agitation overnight at 40° C. The solvent is then evaporated.

The RMN characteristics of this compound are as follows:
RMN $^1$H: (400 MHz, $CD_3DO$) δ (ppm): 8.81 (d, $^{H,P}J$=5.8 Hz, 1H, $H_1$); 7.89 (m, 1H, $H_7$); 7.27-7.12 (m, 12H, $H_5$, $H_6$, $H_{8-17,21,22}$); 6.78-6.75 (m, 1H, $H_4$); 3.52 (s, 3H, $H_{24}$), 3.44 (d, $^2J$=7.3 Hz, 1H, H$_2$), 2.08 (sept, $^2J$=6.6 Hz, 1H, H$_{18}$), 0.69 (d, $^2J$=6.8 Hz, 3H, H$_3$'); 0.56 (d, $^2J$=6.6 Hz, 3H, H$_{3''}$).

RMN $^{31}$P: (162 MHz, CD$_3$DO) δ (ppm): −14.62 (s, 1P).

In an embodiment of a complex according to the invention, the following copper (II) complex III-Cu was synthesized from potassium diphenylphosphinophenyl-azomethinylate Ia-K, according to the following reaction pattern:

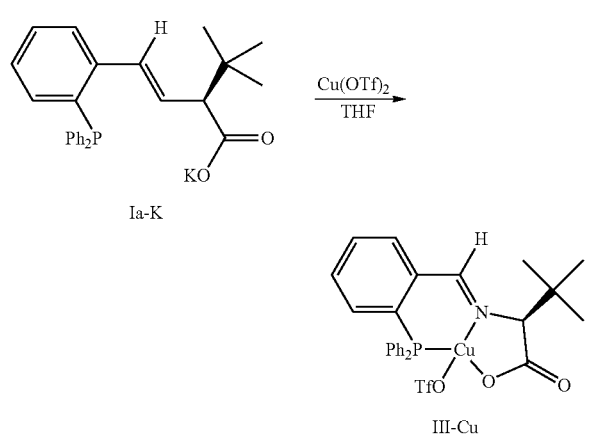

Synthesis of the Compound of Formula III-Cu

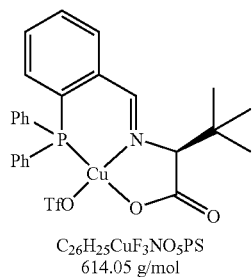

C$_{26}$H$_{25}$CuF$_3$NO$_5$PS
614.05 g/mol

Tert-leucine phosphinoazomethinylate potassium salt (100 mg, 0.23 mmol, 1 eq.) and copper bis-triflate Cu(OTf)$_2$ (114 mg, 0.23 mmol, 1 eq.) are placed in a round-bottom flask. Anhydrous THF is then added (9 mL, 40 mL per mmol). The reaction mixture is agitated at room temperature for 1 hour. The solvent is evaporated and the product is dried under reduced pressure. A green powder is obtained (210 mg, 98%).

The compound Ia-K according to this invention was implemented in addition reactions of 1,4 diethylzinc on 2-cyclohexenone and on 5-methyl-3-hexen-2-one.

In these examples, the following procedure was used.

A copper source such as copper (II) bis-triflate (0.02 mmol, 0.02 eq.), compound Ia-K (0.02 mmol, 0.02 eq.), cyclododecane (internal standard) and an anhydrous solvent (3 mL) are introduced into a Schlenk tube. The mixture is agitated at room temperature for 10 minutes before adding diethylzinc (1.5 mmol, 1.5 eq.). The reaction medium is placed at a temperature of −15° C. and agitated for 5 minutes before the substrate (1 mmol, 1 eq.) is added.

The reaction is stopped by adding 5 mL of a molar solution of hydrochloric acid and the mixture is agitated until it becomes clear. The mixture is diluted with diethyl ether and the organic phase is settled, washed with a saturated sodium chloride solution, dried on magnesium sulfate, filtered and concentrated. The conversion is measured by gas phase chromatography and the enantiomeric excess is determined by chiral gas phase chromatography.

For the addition of 1,4 diethylzinc to 2-cyclohexenone, leading to 3-ethylcyclohexanone, a conversion rate of 98% was observed after 6 hours with an enantiomeric excess of 99%.

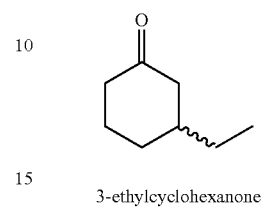

3-ethylcyclohexanone

Lipodex E, 25 m; 50° C. (5 min.) −2° C./min. −110° C. (0 min.) −10° C./min. −160° C. (10 min.); R$_T$(R)=25.4 min.; R$_T$(S)=26.1 min.

For the addition of 1,4 diethylzinc to 5-methyl-3-hexen-2-one, leading to 4-ethyl-5-methylhexan-2-one, a conversion rate of 65% was observed after 14 hours with an enantiomeric excess of 91%.

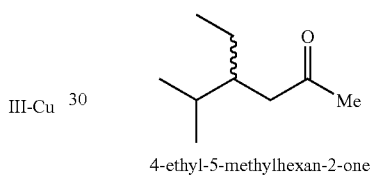

4-ethyl-5-methylhexan-2-one

Lipodex E, 25 m; 50° C. (5 min.) −0.5° C./min −110° C. (0 min.) −10° C./min. −160° C. (10 min.); R$_T$(R)=45.3 min.; R$_T$(S)=47.0 min.

The compound Ia-K according to this invention was also implemented in an acetophenone to 1-phenylethanol reduction reaction by transferring catalyzed hydrides by means of a ruthenium complex RuCl$_2$(PPh$_3$)$_3$. The following procedure was used.

RuCl$_2$(PPh$_3$)$_3$ (0.01 mmol, 0.01 eq.), compound Ia-K according to the invention (0.01 mmol, 0.01 eq.), cyclododecane (internal standard) and anhydrous cold-degassed isopropanol (5 mL) are introduced into a Schlenk tube. The mixture is heated at 80° C. and agitated for 1 hour. After cooling to room temperature, the solution of acetophenone (1 mmol, 1 eq.) in anhydrous isopropanol (2 mL) is added. The reaction medium is heated to 80° C. and the agitation is continued for 15 minutes. After cooling to room temperature, the sodium hydroxide solution (0.25 mmol, 0.25 eq.) in isopropanol (3 mL) is added. The reaction medium is heated to 65° C. and the agitation is continued for 2 hours.

The reaction is stopped by adding 0.5 mL of a molar solution of hydrochloric acid and the mixture is agitated for 5 minutes. The mixture is concentrated and the residue is placed with 10 mL of ethyl acetate and 5 mL of distilled water. The organic phase is settled, washed with a saturated sodium chloride solution, dried on magnesium sulfate, filtered and concentrated. The conversion is measured by gas phase chromatography and the enantiomeric excess is determined by chiral gas phase chromatography.

A conversion rate of 98% was observed after 2 hours with an enantiomeric excess of 48%.

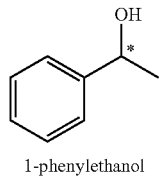

1-phenylethanol

Lipodex E, 25 m; 80° C. (5 min.) −0.7° C./min −130° C. (0 min.) −10° C./min. −160° C. (10 min.); $R_T(R)$=33.8 min.; $R_T(S)$=34.5 min.

The invention claimed is:

1. Compound of formula (I):

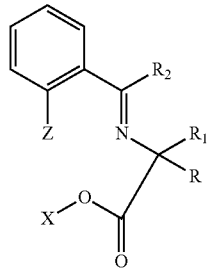

(I)

in which:
X is a hydrogen or an alkaline cation;
R is a C1 to C8 alkyl, or a C5 to C6 cycloalkyl, or an aryl;
$R^1$ is H or a C1 to C8 alkyl, or a C5 to C6 cycloalkyl, or an aryl;
$R^2$ is a hydrogen, or a C1 to C8 alkyl;
Z is a radical with the formula $P(R^{16})_2$ or a radical with the formula $P(O)R^{19}$ in which
$R^{16}$ and $R^{19}$ are independently a C1 to C6 alkyl or a C6 cycloalkyl or an aryl.

2. Compound according to claim 1, characterized in that it is a diphenyl phosphinophenyl azomethinylate.

3. Compound according to claim 2, characterized in that it is chosen from the group consisting of compounds with the formulas:

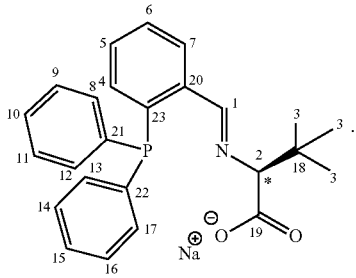

Ia-K

Ia-Na

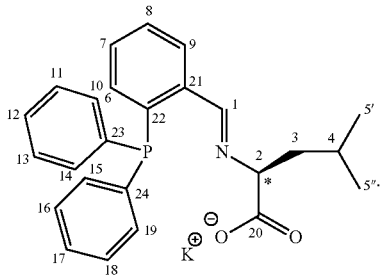

4. Compound according to claim 2, with the formula:

Ib-K

5. Complex of a compound according to claim 1 with at least one metal chosen from the group consisting of copper, palladium, ruthenium, iridium and rhodium.

6. Complex according to claim 5, characterized in that said complex has the formula:

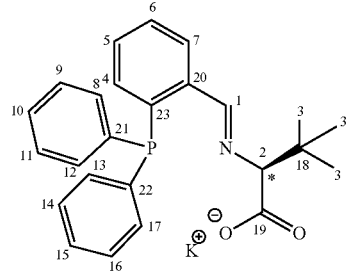

III-Cu

* * * * *